United States Patent [19]

Perronnet et al.

[11] 4,097,578
[45] Jun. 27, 1978

[54] 1-(3'-TRIFLUOROMETHYL-4'-NITRO-PHENYL)-4,4-DIMETHYL IMIDAZOLIDINES

[75] Inventors: Jacques Perronnet; Pierre Girault, both of Paris; Claude Bonne, Bry-sur-Marne, all of France

[73] Assignee: Roussel Uclaf, Paris, France

[21] Appl. No.: 734,557

[22] Filed: Oct. 21, 1976

[30] Foreign Application Priority Data

Oct. 29, 1975   France ................. 75 33084

[51] Int. Cl.² ............... A61K 31/415; C07D 233/72; C07D 233/88
[52] U.S. Cl. ..................... 424/273 R; 548/314
[58] Field of Search ............ 260/309.5, 309.7; 424/273; 548/314

[56] References Cited

U.S. PATENT DOCUMENTS 3,846,441  11/1974  Mine et al. ............. 260/309.5
3,960,883   6/1976  Hubele .................. 260/309.5

FOREIGN PATENT DOCUMENTS 1,354,313  5/1974  United Kingdom ............ 260/309.7

OTHER PUBLICATIONS

Rhone-Poulenc Chem. Abst. 1973, vol. 79, No. 78805s.

Primary Examiner—Natalie Trousof
Attorney, Agent, or Firm—Hammond & Littell

[57] ABSTRACT

Imidazolidines of the formula

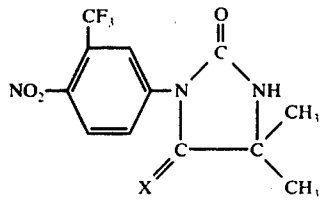

wherein X is selected from the group consisting of oxygen and amine which inhibit the effects of androgens on peripheric receptors without interfering with normal hypophysial functions.

7 Claims, No Drawings

1-(3'-TRIFLUOROMETHYL-4'-NITROPHENYL)-4,4-DIMETHYL IMIDAZOLIDINES

STATE OF THE ART

British Pat. No. 997,037 described imidazolidines of a different structure which have anti-epileptic and anti-convulsant activity.

OBJECTS OF THE INVENTION

It is an object of the invention to provide the novel imidazolidines of formula I and a novel process for their preparation.

It is another object of the invention to provide novel therapeutic compositions which inhibit the effects of androgens.

It is a further object of the invention to provide a method of inducing anti-androgenic activity in warm-blooded animals.

These and other objects and advantages of the invention will become obvious from the following detailed description.

THE INVENTION

The novel imidazolidines of the invention have the formula

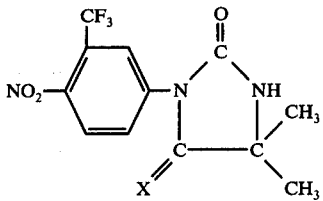

wherein X is selected from the group consisting of oxygen and imine. The compounds are 1-(3'-trifluoromethyl-4'-nitrophenyl)-4,4-dimethyl-imidazoline-2,5-dione and 1-(3'-trifluoromethyl-4'-nitrophenyl)-4,4-dimethyl-5-imino-imidazoline-2-one.

The novel process of the invention for the preparation of the compounds of formula I comprises reacting 2-amino-2-cyano-propane with 3-trifluoromethyl-4-nitrophenyl isocyanate in the presence of a tertiary base to form 1-(3'-trifluoromethyl-4'-nitrophenyl)-4,4-dimethyl-5-imino-imidazoline-2-one which may be recovered or hydrolyzed in an acid media to obtain 1-(3'-trifluoromethyl-4'-nitrophenyl)-4,4-dimethyl-imidazoline-2,5-dione.

The condensation is effected in the presence of a tertiary amine such as pyridine, triethylamine or methyl ethyl pyridine and the condensation is preferably effected in an organic solvent such as tetrahydrofuran, ether or isopropyl ether. The acid for the hydrolysis is preferably hydrochloric acid or sulfuric acid.

The novel antiandrogenic compositions of the invention are comprised of an effective amount of at least one compound of formula I and an inert pharmaceutical carrier. The compositions may be in the form of injectable solutions or suspensions, tablets, coated tablets, capsules, syrups, suppositories, creams, pomades and lotions.

The excipient or pharmaceutical carrier may be aqueous or non-aqueous vehicles, talc, arabic gum, lactose, starch, magnesium stearate, cacao butter, fatty bodies of animal or vegetable origin, paraffinic derivatives, glycols, preservatives, diverse wetting agents, dispersants or emulsifiers.

The compositions due to their antiandrogenic activity without interference with hypophysial functions are useful for the treatment of adolescents without interfering with growth and for the treatment of adults without the problems of chemical castration. They are useful for the treatment of adenomea and neoplasia of the prostate, of hirsutism, of acne, of seborrhea and of hyperpilosity.

The novel method of the invention of inducing antiandrogenic activity in warm-blooded animals, including humans, comprises administering to warm-blooded animals an antiandrogenically effective amount of at least one compound of formula I. The compounds may be administered orally, rectally, topically, perlingually or parenterally. The usual daily dose is 2 to 100 mg/kg depending on the method of administration and the compounds.

In the following examples there are described several preferred embodiments to illustrate the invention. However, it is to be understood that the invention is not intended to be limited to the specific embodiments.

EXAMPLE 1

1-(3'-trifluoromethyl-4'-nitrophenyl)-4,4-dimethyl-5-iminoimidazoline-2-one 1 ml of triethylamine was added to a mixture of 49.6g of 3-trifluoromethyl-4-nitrophenyl isocyanate in 500 ml of tetrahydrofuran and then 18 g of 2-amino-2-cyano-propane were rapidly added thereto. The mixture was stirred for 72 hours at 20° C and was evaporated to dryness under reduced pressure. The residue was chromatographed over silica gel and was eluted with an 8-2 methylene chloride-acetone mixture to obtain 27 g of 1-(3'-trifluoromethyl-4'-nitrophenyl)-4,4-dimethyl-5-imino-imidazoline-2-one melting at 168° C.

Analysis: $C_{12}H_{11}F_3N_4O_3$. Calculated: %C, 45.57; %H, 3.50; %N, 17.71. Found: C, 45.6; H, 3.6; N, 17.5.

IR Spectrum (chloroform): absorption at 3442 $cm^{-1}$, characteristic of NH; at 1755 $cm^{-1}$, characteristic of C = O, at 1673 $cm^{-1}$, characteristic of C = N; at 1615 and 1595 $cm^{-1}$, characteristic of aromatic ring and at 1542, 1492 and 1355 $cm^{-1}$, characteristic of $NO_2$.

EXAMPLE 2

1-(3'-trifluoromethyl-4'-nitrophenyl)-4,4-dimethyl-imidazoline-2,5-dione

A suspension of 10 g of 1-(3'-trifluoromethyl-4'-nitrophenyl)-4,4-dimethyl-5-imino-imidazoline-2-one, 35 ml of 22° Be aqueous hydrochloric acid and 35 ml of water was refluxed for an hour, cooled to 20° C and poured into water. The mixture was vacuum filtered and the recovered precipitate was washed and dried to obtain 9.5 g of 1-(3'-trifluoromethyl-4'-nitrophenyl)-4,4-dimethyl-imidazoline-2,5-dione melting at 149° C. A microanalytical sample after crystallization from ethanol melted at 149° C.

Analysis: $C_{12}H_{10}F_3N_3O_4$. Calculated: %C 45.43; %H 3.17; %F, 17.96; %N 13.24. Found: C, 45.5; H, 3.4; F, 17.9; N, 12.9.

IR Spectrum (chloroform): absorption at 3438 $cm^{-1}$ characteristic of NH; at 1792 and 1734 $cm^{-1}$, characteristic of C = O, at 1613, 1597 and 1501 $cm^{-1}$ characteristic of aromatic ring and at 1545, 1358 and 1359 $cm^{-1}$ characteristic of $NO_2$.

EXAMPLE 3

Tablets were prepared from 100 mg of the product of Example 2 and sufficient excipient of lactose, starch, talc and magnesium stearate for a final weight of 300 mg.

PHARMACOLOGICAL STUDY

Test A: Antiandrogenic activity in rats

This test was effected on groups of 5 male rats of the Sprague-Dawley strain weighing 75 ± 5 g castrated by the scrotal method while anesthesied with ether. The rats daily simultaneously received subcustaneously for 7 days testosterone propionate at 50 μg/rat/day and 1-(3'-trifluoromethyl-4'-nitrophenyl)-4,4-dimethyl-imidazoline-2,5-dione at 1 mg/day/rat. The products were in solution in a volume or 0.1 ml of sesame oil containing 5% of benzyl alcohol. The rats were killed 24 method hours after the last administration and the prostate and seminal vesicules were removed and placed for 24 hours in an isotonic saline solution containing 10% formol. The organs were then dissected and weighed to determine the inhibition of weight increase of the genital organs induced by the androgen which indicates the antiandrogenic activity of the test compound. The variations of the weight of the prostate or seminal vesicules was homogenized by logarithimic transformation by the method of Bartlett [J. Roy. Stat. Soc., 1937, Supp. 4, p. 137] and this homogeneity was verified by the Bartlett test [Biometrics, Vol. 3 (1947), p. 39]. The results were analyzed by factorial analysis and are reported in Table I.

TABLE I

| Group | Weight of Seminal Vesicules in mg | Weight of Ventral prostate in mg |
|---|---|---|
| Controls | 11.5 ± 0.9 | 16.8 ± 1.0 |
| Testosterone propionate | 79.6 ± 8.1 | 90.3 ± 7.0 |
| Test Compound | 12.3 ± 0.8 | 15.0 ± 1.3 |
| Testosterone Propionate + Test Compound | 17.2 ± 2.9* | 45.0 ± 4.3* |

*Factorial analysis p≦0.01

The data of Table I shows that the compound of Example 2 provokes a 92% inhibition of the weight increase of the seminal vesicules and a 61% inhibition of weight increase of the prostate which indicates good antiandrogenic activity against testosterone propionate.

The test was repeated with the product of Example 1 and the results are reported in Table II.

TABLE II

| Group | Weight of Seminal Vesicules in mg | Weight of Prostate in mg |
|---|---|---|
| Controls | 7.7 ± 0.7 | 11.9 ± 0.7 |
| Testosterone propionate | 100.3 ± 6.1 | 105.6 ± 5.0 |
| Compound of Ex. 1 | 10.9 ± 1.1 | 14.5 ± 0.4 |
| Testosterone propionate + product of Ex. 1 | 29.1 ± 3.5* | 66.3 ± 5.5* |

*Factorial analysis p ≦0.01

The results of Table II show that the product of Example 1 provoked an inhibition of 77% of weight increase of seminal vesicules and a 43% inhibition of prostate weight increase which indicates good antiandrogenic activity against testosterone propionate.

B. Inhibition of prostatic incorporation of radioactivity after injection of a trace dose of H³-testosterone in castrated rats Groups of 3 male rats of the Sprague-Dawley SPF strain weighing 70 ± 10 g were castrated 24 hours before receiving a subcutaneous injection of 5 mg of the test product. 16 hours later, the animals received an intramuscular injection of 10μ Ci/100 g of 1α-H³-testosterone (26 Ci/mmol) in an alcoholic solution and the animals were killed one hour after the hormone injection. The ventral prostate was removed, rinsed with an isotonic sodium chloride solution, weighed and then was solubilized by alkaline digestion. The radioactivity of the samples were measured after addition of 15 ml of sparkling liquid and the results are reported in Table III as a percentage of inhibition of testosterone incorporation. dpm/mg = disintegration per minute per mg of fresh prostatic tissue.

TABLE III

| Product | Incorporation dpm/mg | % of Inhibition |
|---|---|---|
| Controls | 114 ± 4 | — |
| Example 2 | 35 ± 8 | 68 |
| Example 1 | 80 ± 9 | 42 |
| Controls | 138 ± 8 | — |

The results of Table III show that the 2 products diminish the incorporation of the hormone in the prostate.

Various modifications of the product and processes of the invention may be made without departing from the spirit or scope thereof and it should be understood that the invention is to be limited only as defined in the appended claims.

We claim:
1. A compound of the formula

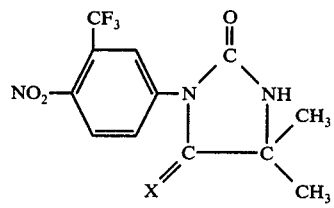

wherein X is selected from the group consisting of oxygen and imine.

2. A compound of claim 1 which is 1-(3'-trifluoromethyl-4'-nitrophenyl)-4,4-dimethyl-5-imino-imidazoline-2-one.

3. A compound of claim 1 which is 1-(3'-trifluoromethyl-4'-nitrophenyl)-4,4-dimethyl-imidazoline-2,5-dione.

4. An antiandrogenic composition comprising an antiandrogenically effective amount of at least one compound of claim 1 and an inert pharmaceutical carrier.

5. A method of inducing antiandrogenic activity in warm-blooded animals comprising administering to warm-blooded animals an antiandrogenically effective amount of claim 1.

6. The method of claim 5 wherein the compound is 1-(3'-trifluoromethyl-4'-nitrophenyl)-4,4-dimethyl-5-iminoimidazoline-2-one.

7. The method of claim 5 wherein the compound is 1-(3'-trifluoromethyl-4'-nitrophenyl)-4,4-dimethyl-imidazoline-2,5-dione.

* * * * *